United States Patent [19]

Redikultsev et al.

[11] 4,302,545

[45] Nov. 24, 1981

[54] APPARATUS FOR CHEMICAL FROTH SUPPRESSION IN A FERMENTER

[76] Inventors: Jury V. Redikultsev, mikroraion "G", 19, kv. 113; Leonid A. Litvinenko, mikroraion "AB", 8, kv. 74; Valery A. Sedov, mikroraion "G", 1, kv. 15, all of, Moskovskaya oblast, Puschino, U.S.S.R.

[21] Appl. No.: 113,475

[22] Filed: Jan. 21, 1980

[30] Foreign Application Priority Data

Jan. 19, 1979 [SU] U.S.S.R. .............................. 2706012

[51] Int. Cl.$^3$ .............................................. C12M 1/36
[52] U.S. Cl. .................................... 435/289; 55/178; 252/361; 435/812
[58] Field of Search ..................... 435/289, 291, 812; 55/178; 252/361

[56] References Cited

U.S. PATENT DOCUMENTS

| | | | |
|---|---|---|---|
| 1,916,614 | 7/1933 | Harrison | 435/812 X |
| 2,948,351 | 8/1960 | Phillips et al. | 252/361 X |
| 3,317,435 | 5/1967 | Yamashita et al. | 252/361 |
| 3,354,050 | 11/1967 | Rungaldier et al. | 435/812 X |
| 4,003,724 | 1/1977 | Payne et al. | 55/87 |
| 4,009,118 | 2/1977 | Laiho | 55/178 X |

FOREIGN PATENT DOCUMENTS

| | | | |
|---|---|---|---|
| 572759 | 10/1945 | United Kingdom | 435/812 |
| 623863 | 8/1978 | U.S.S.R. | 435/812 |

*Primary Examiner*—Robert J. Warden
*Attorney, Agent, or Firm*—McAulay, Fields, Fisher, Goldstein & Nissen

[57] ABSTRACT

An apparatus for chemical froth suppression in a fermenter comprises a froth sensor installed in the fermenter for tracing the froth and a vessel containing a chemical froth suppressor which is fed to the froth sensor and to the fermenter. The froth sensor comprises a hollow chamber accommodating a throttle and a nozzle. The chamber has a through opening with the walls having two ports congruent to and coaxial with the outlet orifice of the nozzle, through which passes a jet of the froth suppressor leaving the outlet orifice of the nozzle to fly past the through opening and to get into the chamber to be reflected from its concave wall for being removed into the vessel containing the chemical froth suppressor.

2 Claims, 2 Drawing Figures

APPARATUS FOR CHEMICAL FROTH SUPPRESSION IN A FERMENTER

FIELD OF THE ART

The invention relates to apparatus for chemical froth suppressors, and more particularly, to apparatus for chemical froth suppression in fermenters.

The invention may be used in the microbiological, medical and chemical industries and in research applications.

BACKGROUND OF THE INVENTION

Steady froth formation is an undesirable phenomenon occurring in aerating media containing organic matter. Stability of froth is associated with the composition of complex media or products of metabolism of microorganisms which are not identified in many instances, and the fight against froth formation is frequently conducted on an empirical basis.

Negative effect of froth formation consists in the following:

- a culture with froth may be let out of the fermenter through air outlet ports;
- the value of $KL_a$ (efficiency of oxygen absorption) decreases;
- in chemostatic cultures (cultures with complete stirring to which a culture medium is added at a constant rate and from which a culture is taken-off at the same rate while retaining the total volume unchanged) the gas content changes, hence the liquid volume becomes uncontrollable.

Froth formation is generally prevented by using froth suppressors which may be classified in the following manner:

- elimination of froth-forming substances and action on the froth with physico-chemical facilities;
- destruction of froth by mechanical, hydro- and aero-dynamic methods;
- acoustic froth suppression using audio and ultrasonic frequency oscillations;
- thermal froth suppression using saturated steam or heated liquid;
- electrical froth suppression;
- stabilization of froth level and temporary suspension of air supply for aeration or temporary suspension of mechanical stirring or discharge of excessive froth from the apparatus;
- combined methods.

Among all the above-mentioned froth suppressors only chemical and mechanical ones have found a widespread use in the microbiological industry since all remaining froth suppressors are poorly studied and not applied in practice for various reasons. Thus, the works on the use of ultrasonic oscillations for froth suppression are still at the laboratory stage and, according to preliminary estimations, this method for suppressing large quantities of froth in fermenters are bound to prove economically inefficient. The use of thermal froth suppressors is limited by the sensitivity of many microorganisms to high temperature, while the knowledge of the influence of electric field, especially of $\alpha$-particles on microorganisms is still inadequate so that their use in the microbiological applications is limited.

Various mechanical froth suppressors are recommended.

One of the simplest modifications consists in using a rapidly rotating rotor (cf. British patent specification No. 8,922,505, Cl. 14(2)L, publ. in 1962).

Such froth suppressors are generally mounted in a confining device of the cyclone type which can be connected to a vacuum chamber.

The prior art teaches a mechanical froth suppressor comprising a perforated plate having two impellers installed thereon of which one—the upper impeller—is arranged with the vanes up and the other—the lower impeller—is arranged with the vanes down. For destructing froth over the liquid surface, there is provided a turbine rotating about its axis so that during rotation of the turbine an ascending gas flow is formed under the turbine, which takes-in the froth to be thrown away by the turbine blades in the form of liquid jets. The working member comprises a perforated plate submerged in the froth and connected with a vibratory drive (cf. U.S. Pat. No. 2,610,155, publ. in 1962). Known in the art is an apparatus for mechanical froth suppression, comprising a rotary perforated plate having partitions in the form of hollow truncated cones mounted on the plate with spaces therebetween for the passage of liquid (cf. USSR Inventor's Certificate No. 107900, Cl. C 12B 1/18, publ. in the Off. Bull. No. 9, 1957, page 16).

An apparatus for froth suppression, comprising a stack of conical plates on a hollow shaft is widely used in practice (cf. Swiss Pat. No. 1660, publ. in 1968).

The apparatus is installed on an independent shaft. The apparatus are used both in laboratory and commercial installations.

Known in the art is a mechanical blade froth suppressor with a horizontally extending working shaft. To improve the efficiency of froth suppression, a partition wall is provided inside the froth suppressor vessel to divide the vessel into two communicating compartments, one compartment having at the bottom thereof a pipe having its inlet end arranged immediately under impellers, and the outlet end is incorporated in the partition wall (cf. USSR Inventor's Certificate No. 246446, Cl. C 12C, publ. in the Off. Bull. No. 21, 1969, page 10).

A hydraulic and pneumatic system for collecting, removing and destructing froth was contemplated, featuring recirculation of concentrated solution and having two pumps. Froth suppression is effected by means of pumps, one pump being designed for processing gas and liquid emulsions. A portion of waste gas is fed for recirculation for pneumatic froth suppression. The second pump takes-off the liquid from the settling basin and also feeds it for recirculation (cf. U.S. Pat. No. 3,339,345, Cl. 55-178, publ. in 1967).

All above-described froth suppressors are rarely used in the microbiological applications in spite of their large structural variety. Such apparatus either cannot provide for complete suppression of froth or they impose considerable power requirements. In addition, such systems are cumbersome and do not permit the useful space of the fermenter to be completely utilized so that the filling ratio of fermenters is from 0.5 to 0.6 of the total volume. The free space is used for compensation of the level rise which generally does not exceed 10% owing to gas content after the aeration is put on, and also for controlling the froth level.

Automatic control of processes occurring during cultivation of microorganisms, including the froth suppression process, is very important for operation of fermenters. In principle, this problem should be very simple to resolve: a mechanical stirrer and an actuator for adding a chemical froth suppressor are to be mounted in the fermenter, the devices being operable by means of a mechanism actuated in response to the presence of froth above an admissible level. A simple solution resides in an installation of a sensor—a contact electrode—at a preset level producing a signal when the froth is in contact with the electrode. Not every froth is, however, electrically conducting. A-c or d-c voltage of 10-30 V is fed for the electrode supply and a current of 5 to 20 mA and over flows through the froth. In case d-c supply is used, such voltage and amperage cause polarization of the electrode so that its sensitivity appreciably changes during fermentation. The use of alternating current results in erosion of the electrode, while metal ions getting to the culture liquor negatively affect the process of cultivation of microorganisms.

The use of electrodes is not always justified as a comparably large area of contact of the forth with electrode is required, and the froth sticking to the electrode causes changes in its operating parameters.

Therefore, various contactless froth level indicators have been contemplated. Photocells are in a widespread used (cf. USSR Inventor's Certificate No. 128827, Cl. C 12 B 1/18, publ, in the Off. Bull., No. 11, 1960) incorporated in the fermenter wall, which, after the froth cuts-off the light beam, turn on actuators, such as an electric motor of a gear pump for feeding a chemical suppressor.

Culture media generally contain various quantities of mineral salts which, after dissolution, form relatively well electrically conducting froth having various electrical resistance. Therefore a contact electrode was contemplated for indicating the froth level (cf. M. Zh. Kristapsons, L.Ya. Latsis, Coll, or Art. "Controlled Microbeal Synthesis" (in Russian), Riga, Znanie Publ., 1973), to be inserted in an arm of a bridge circuit. This enables the electrode supply with an a-c voltage of 0.2 V so that maximum current flowing through the froth does not exceed 100 $\mu$A. Such amperage and voltage cannot have any negative influence in the microbiological process and life activity of microorganisms.

An interesting solution involves the installation of a contact electrode on a float which is movable up and down depending on the froth level (cf. GDR Pat. No. 76454, Cl C 12 B, publ. in 1970).

The use of apparatus for chemical froth suppression enables more efficient control of froth formation thereby improving the filling ratio of a fermenter. It should be, however, noted that the control of froth suppressor flow rate requires additional systems which are sophisticated expensive in the manufacture and do not always comply with the requirements imposed by microorganism cultivation conditions; besides they do not exclude overconsumption of froth suppressor.

Also known in the art is an apparatus for chemical froth suppression in a fermenter having a froth sensor tracing the froth in the fermenter, and a vessel containing a chemical suppressor which is fed to the fermenter by means of a pneumatic pump along a take-off pipe (cf. Technical Description and Operation Manual "Complex of Cultivation Equipment" (in Russian), SKB Biologicheskogo priborostroenia AN SSSR, Pushchino, 1978, pp. 37-40).

In this apparatus, the froth sensor comprises a capillary tube installed in the interior of the fermenter at a preset level and connected by means of a pipeline to a sensor member having a magnetic contact. Another pipeline connecting the sensor member to the interior of the fermenter is provided with a pump for pumping air along the resultant closed circuit.

The apparatus also comprises an actuating mechanism having a vessel containing a chemical froth suppressor provided with a take-off pipe having a pinch valve for feeding the froth suppressor from the vessel containing the chemical froth suppressor to the fermenter following a signal from the sensor member.

The apparatus functions in the following manner.

When froth in the fermenter does not touch the opening of the capillary tube, the pump pumps a gas mixture from the fermenter through the capillary tube and sensor member to return it back to the fermenter. The sensor member is so adjusted that its membrane having a permanent magnet secured thereto is stationary, the magnetic contact is open, and the pinch valve of the actuating mechanism is closed. When the froth approaches the opening of the capillary tube, the pump starts feeding the froth, the resistance of the capillary tube abruptly increases so that the pump causes a pressure reduction in the sensor member. The membrane starts displacing until the magnetic contact is closed, to open the pinch valve for feeding a froth suppressor. The froth suppressor is admitted to the fermenter to destruct the froth thereby cleaning the capillary tube so that the resistance of the capillary tube again decreases, and the sensor member returns back to its initial position to open the magnetic contact. The pinch valve is again closed to interrupt the admission of the chemical froth suppressor to the fermenter.

This apparatus for chemical froth suppression may be used in both commerical and laboratory fermenters.

The provision of the gas circulation circuit passing through the sensor member which becomes a focus of decay for microorganisms when clogged with froth breaks the septic conditions of microbiological process. In addition, pulse feeding of froth suppressor to the fermenter does not exclude overconsumption of froth suppressor as the process of froth formation cannot be forecast by a researcher. The absence of stirring of froth suppressor causes its stratification thereby changing the character of its action on the froth layer.

SUMMARY OF THE INVENTION

It is an object of the invention to provide a structurally simple apparatus for chemical froth suppression in a fermenter which is capable of stabilizing a froth layer at any preset level with a chemical froth suppressor without overconsumption of the froth suppressor.

Another object of the invention is to prevent stratification of froth suppressor.

This is accomplished by that in an apparatus for chemical froth suppression, comprising a froth sensor for tracing the froth in the fermenter and a vessel containing a chemical froth suppressor which is fed to the fermenter by means of a pneumatic pump through a take-off pipe, according to the invention, the froth sensor is installed in the fermenter and comprises a throttle and a nozzle installed in series one downstream the other in the direction of flow of the chemical froth suppressor downstream the pneumatic pump and connected thereto, and a hollow chamber which accommodates the throttle and the nozzle, communicates, via a drain pipe, with the vessel containing the chemical froth suppressor and has a through opening, the walls of the opening having two ports congruent to and coaxial with an outlet orifice of the nozzle, through which passes a jet of the froth suppressor leaving the outlet orifice of the nozzles to fly past the through opening and to get into the chamber, the wall of the chamber arranged opposite to the port most distant from the nozzle being concave to reflect the jet of the froth suppressor and to remove it through the drain pipe to the vessel containing the chemical froth suppressor.

The outlet orifice of the nozzle is preferably arranged at about the level of froth in the fermenter, and the concave wall of the chamber is arranged above the outlet orifice.

This construction of the apparatus for chemical froth suppression in the fermenter according to the invention enables an automatic tracing of froth and its stabilization owing to the feeding of a froth suppressor to the froth layer necessary to maintain a preset height of froth independent of the rate and time of froth formation. In addition, permanent circulation of froth suppressor prevents it from stratifying thus ensuring more stable action of froth suppressor on the froth, improving reliability of operation of the apparatus and lowering the cost.

BRIEF DESCRIPTION OF THE DRAWINGS

These and other objects of the invention will become apparent from reading the following description of specific embodiments thereof with reference to the accompanying drawings, in which.

DETAILED DESCRIPTION OF THE INVENTION

Figure 1:
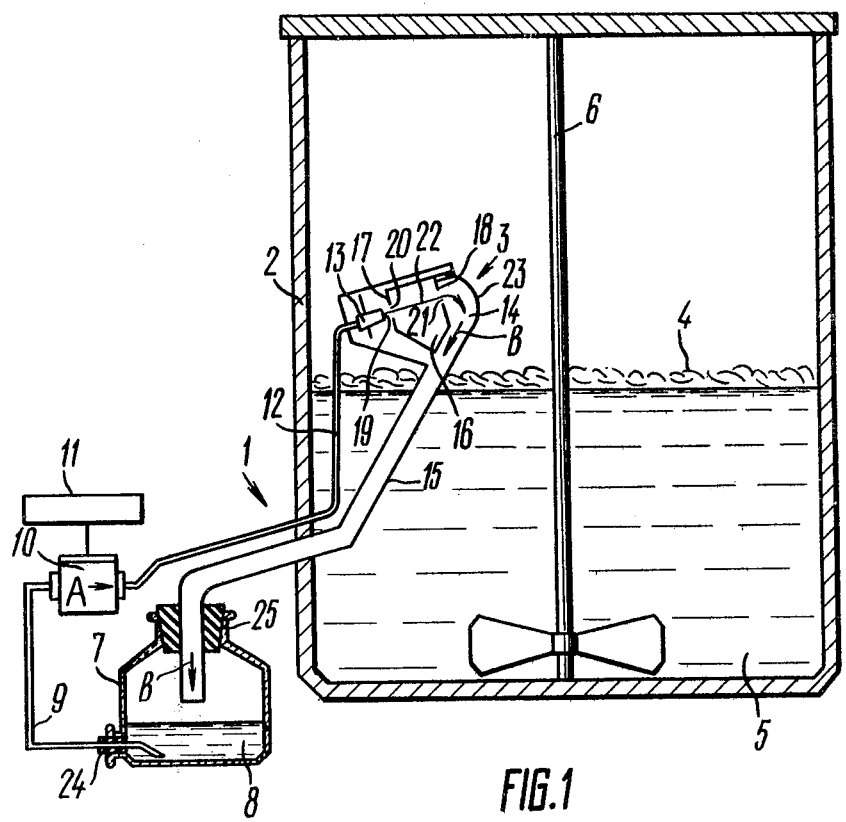
FIG. 1 is a general diagrammatic view (in longitudinal section) of an apparatus for chemical froth suppression in a fermenter, according to the invention.

An apparatus 1 (FIG. 1) for chemical froth suppression in a fermenter 2, according to the invention, comprises a froth sensor 3 installed in the fermenter 2 for tracing a froth 4 which is formed therein as a result of a fermentation process occurring in a culture medium 5 stirred by means of a stirrer 6 of the fermenter 2.

The apparatus 1 also comprises a vessel 7 containing a chemical froth suppressor 8 which is fed to the sensor 3 of the froth 4 as shown by arrow A along a take-off pipe 9 by means of a well known pneumatic pump 10 which is pneumatically coupled to a well known pneumatic pulse generator 11.

The sensor 3 of the froth 4 comprises a throttle 12, a nozzle 13 and a hollow chamber 14. The throttle 12 and the nozzle 13 are mounted in series one downstream the other in the direction of flow of the froth suppressor 8 downstream the pneumatic pump 10 and are connected thereto. The nozzle 13 is installed within the hollow chamber 14.

The hollow chamber 14 is connected by means of a drain pipe 15 to the vessel 7 containing the chemical froth suppressor 8 and has a through opening 16. Walls 17 and 18 of the opening 16 have two ports 20 and 21 congruent to and coaxial with an outlet orifice 19 of the nozzle 13, through which passes a jet 22 of the froth suppressor 8 leaving the outlet orifice 19 of the nozzle 13 to fly past the through opening 16 and to get into the chamber 14.

A wall 23 of the chamber 14 arranged opposite to the port 21 most distant from the nozzle 13 is concave to reflect the jet 22 of the froth suppressor 8 and to remove it as shown by arrow B through the drain pipe 15 to the vessel 7 containing the chemical froth suppressor 8 so as to form a closed circuit for circulation of the froth suppressor 8.

In this embodiment of the apparatus 1 the outlet orifice 19 of the nozzle 13 is arranged somewhat above the level of the froth 4, and the concave wall 23 of the chamber 14 is above the outlet orifice 19.

The take-off pipe 9 and the drain pipe 15 are secured in the vessel 7 containing the chemical froth suppressor 8 using gaskets 24 and 25, respectively.

Figure 2:
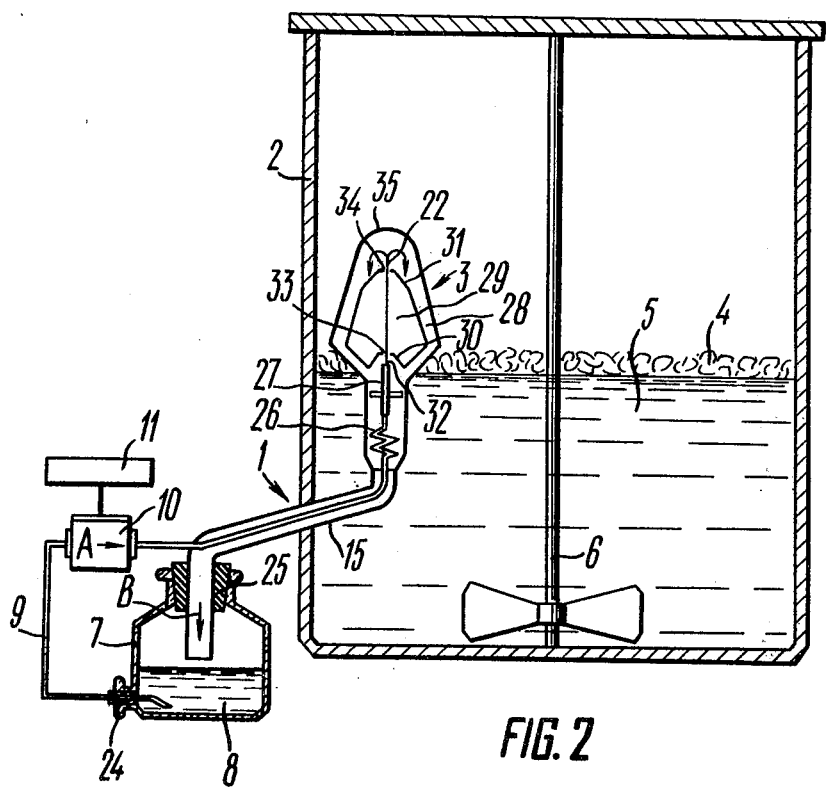
FIG. 2 is another embodiment (in longitudinal section) of the apparatus according to the invention.

The apparatus 1 shown in FIG. 2 is most efficient for suppressing froth in the fermenter 2.

The apparatus 1 shown in FIG. 2 is similar to the apparatus 1 of FIG. 1, and only some structural differences relating to the sensor 3 of the froth 4 will be described below.

In this embodiment the sensor 3 of the froth 4 comprises a throttle 26, a nozzle 27 and a hollow chamber 28. The throttle 26 and the nozzle 27 are installed in series one downstream the other downstream the pneumatic pump 10 in the direction of flow of the froth suppressor 8 in the hollow chamber 28.

The hollow chamber 28 is connected by means of the drain pipe 15 to the vessel 7 containing the chemical froth suppressor 8 and has a through opening 29. Walls 30 and 31 of the opening 29 have two ports 33 and 34 congruent to and coaxial with an outlet orifice 32 of the nozzle 27, through which passes the jet 22 of the froth suppressor 8 leaving the nozzle 27 to fly past the opening 29 and to get into the chamber 28. A wall 35 of the chamber 28 arranged opposite to the port 34 most distant from the nozzle 27 is concave to reflect the jet 22 of the froth suppressor and to remove it as shown by arrow B through the drain pipe 15 to the vessel 7 containing the chemical froth suppressor 8 thus enabling, similarly to the apparatus 1 of FIG. 1, the provision of a closed circuit for circulation of the froth suppressor 8.

In this embodiment of the apparatus 1 the outlet orifice 32 of the nozzle 27 is arranged at the level of the froth 4 and the concave wall 35 of the chamber 28 is arranged above the outlet orifice 32.

Operation of the apparatus 1 for chemical froth suppression in the fermenter 2 is the same for the embodiments shown in FIGS. 1 and 2 and based on the use of the jet 22 of the chemical froth suppressor 8 moving freely along a preset path and changing the flying path upon touching the froth 4.

The chemical froth suppressor 8 is pumped from the vessel 7 along the take-off pipe 9 by means of the pneumatic pump 10 to the throttle 12 (26) and leaves its outlet orifice 19 (32) in the form of the jet 22. The jet 22, if it does not touch the froth 4 flies past the opening 16 (29) to get into the chamber 14 (28) wherein it is reflected from its wall 23 (25) and is removed through the drain pipe 15 to the vessel 7 thus forming a closed circuit for circulation of the froth suppressor 8. The contact of the froth 4 with the jet 22 of the froth suppressor results in a change in the flying path of the jet 22, which gets in the froth 4 to suppress it. (The reference numerals in the parentheses are given for the embodiment shown in FIG. 2).

The useful result of the invention resides in that the feeding of froth suppressor to the froth occurs owing to the direct contact of the froth with the outflowing jet of the chemical froth suppressor thus preventing overconsumption of froth suppressor and enabling stabilization of the fermentation process in terms of the froth height. Permanent closed circulation of froth suppressor prevents it from stratifying. Simplicity of manufacture and reliability in operation ensure widespread application of the apparatus according to the invention for chemical froth suppression in a fermenter.

Specific and narrow terminology was used for the description of the specific embodiments of the invention. The invention is not, however, limited by the terms used, and it should be born in mind that each term covers all equivalent elements having the same function and used for accomplishing the same object.

Through the invention has been described as applied to the preferred embodiment thereof, it is understood that various modifications and changes may be introduced without departure from the spirit and scope of the invention as will be readily apparent to those skilled in the art. Such modifications and changes will be considered as not deviating from the spirit and scope of the appended claims.

What is claimed is:

1. An apparatus for chemical froth suppression in a fermenter, comprising:
   a vessel containing a chemical froth suppressor;
   a take-off pipe connected to said vessel;
   a pneumatic pump connected to said take-off pipe for taking-off said froth suppressor from said vessel along said take-off pipe;
   a pneumatic pulse generator pneumatically coupled to said pneumatic pump to drive said pump continuously during operation of said fermenter; and
   a froth sensor installed in said fermenter for tracing the froth which is formed therein as a result of a process occurring in the fermenter, said froth sensor comprising a throttle installed downstream from said pneumatic pump in the direction of flow of said chemical froth suppressor and connected thereto, a nozzle having an outlet orifice from which a jet of said froth suppressor flows and which is installed downstream of said throttle, and in fluid connection therewith, in the direction of flow of said chemical froth suppressor and a hollow chamber accommodating said throttle and nozzle, whereby the jet of froth suppressor flowing from said nozzle traverses said hollow chamber when no froth is present, and contacts said froth, when froth is present within the hollow chamber, and having a drain pipe at the opposite side of said hollow chamber, said drain pipe being connected to said chemical froth suppressor and having a through opening formed by first, second, and third walls, a first port in the first wall of said through opening, which is congruent to and coaxial with said outlet orifice of said nozzle, a second port in the third wall of said through opening, which is congruent to and coaxial with the first port, said jet of said froth suppressor passing through said ports after leaving said nozzle to fly past said through opening and into said hollow chamber, having a concave wall arranged opposite to said second port and reflecting said jet of said froth suppressor and removing it through said drain pipe to said vessel containing said chemical froth suppressor thereby forming a closed circuit for circulation of said chemical froth suppressor when froth is below the level of the jet in said hollow chamber.

2. An apparatus according to claim 1, wherein said outlet orifice of said nozzle is arranged approximately above the normal level of said froth in said fermenter; said concave wall of said hollow chamber being arranged above said outlet orifice.

* * * * *